US008003608B2

(12) United States Patent
Luger

(10) Patent No.: US 8,003,608 B2
(45) Date of Patent: Aug. 23, 2011

(54) INFLAMMATION-INHIBITING COMPOUNDS

(75) Inventor: Thomas Luger, Muenster (DE)

(73) Assignees: Thomas Luger, Münster (DE); Stephan Grabbe, Münster (DE); Thomas Brzoska, Münster (DE)

(*) Notice: Subject to any disclaimer, the term of this patent is extended or adjusted under 35 U.S.C. 154(b) by 644 days.

(21) Appl. No.: 10/467,993

(22) PCT Filed: Feb. 8, 2002

(86) PCT No.: PCT/EP02/01323
§ 371 (c)(1),
(2), (4) Date: Sep. 26, 2003

(87) PCT Pub. No.: WO02/064131
PCT Pub. Date: Aug. 22, 2002

(65) Prior Publication Data
US 2004/0077552 A1 Apr. 22, 2004

(30) Foreign Application Priority Data
Feb. 14, 2001 (DE) .................. 101 06 852

(51) Int. Cl.
*A61K 38/34* (2006.01)
*C07K 14/68* (2006.01)

(52) U.S. Cl. ...................................................... 514/10.7

(58) Field of Classification Search ........................ None
See application file for complete search history.

(56) References Cited

U.S. PATENT DOCUMENTS

| 5,614,520 A | * | 3/1997 | Kondo et al. | 514/236.8 |
| 5,939,394 A | * | 8/1999 | Fleming et al. | 514/23 |
| 6,117,896 A | * | 9/2000 | Qabar et al. | 514/384 |
| 6,245,790 B1 | * | 6/2001 | Hattori et al. | 514/365 |

FOREIGN PATENT DOCUMENTS

| EP | 0 934 924 | | 8/1999 |
| FR | 2 784 028 | | 4/2000 |
| WO | WO88/00833 | | 2/1988 |
| WO | WO 89/09226 | * | 3/1988 |
| WO | WO 89/09226 | * | 8/1989 |
| WO | WO89/09226 | | 10/1989 |
| WO | WO96/23490 | | 8/1996 |
| WO | WO96/27371 | | 9/1996 |
| WO | WO 97/45117 | * | 12/1997 |

OTHER PUBLICATIONS

What is Psoriasis? http://www.skincarephysicians.com/psoriasisnet/whatis.ht.*
Mesri EA., "Inflammatory reactivation and angiogenicity of Kaposi's sarcoma-associated herpesvirus/HHV8: a missing link in the pathogenesis of acquired immunodeficiency syndrome-associated Kaposi's sarcoma.Blood," Jun. 15, 1999;93(12):4031-3.*
Portanova JP, et al, "Selective neutralization of prostaglandin E2 blocks inflammation, hyperalgesia, and interleukin 6 production in vivo," J Exp Med. Sep. 1, 1996;184(3):883-91.*
Kalden DH, et al "Mechanisms of the antiinflammatory effects of alpha-MSH. Role of transcription factor NF-kappa B and adhesion molecule expression," Ann N Y Acad Sci. Oct. 20, 1999;885:254-61.*
Uehara Y, et al "The dipeptide Lys-Pro attenuates interleukin-1 beta-induced anorexia," Peptides. Mar.-Apr. 1993;14(2):175-8.*
Rajora N, et al, "Alpha-MSH modulates experimental inflammatory bowel disease," Peptides. 1997;18(3):381-385.*

Merck Manual Colitis Docuiment Name Merck(2010) found at http://www.merckmanuals.com/home/ search.html?qt=colitis& qp=%2Bsite%3Awww%2Emerckmanuals%2Ecom+%2Burl%3A% 2Fhome+%2Durl%3Aprint%2F+%2Durl%3Aindex% 2F+%2D url% 3Aresources% 2Fpronunciations+%2 Durl%3Amultimedia+ 2F+%2 Durl%3A%2Fhome%2Fau+%2Durl%3A%2 Fhome%2Fag+& charset=utf8&la=en&start=0.*
Oluyomi, A.O., et al., "Antinociceptive activity of peptides related to interleukin-1β-(193-195), Lys-Pro-Thr" European Journal of Pharmacology 1994; 258: 131-138.
Database CA Online, Chemical Abstracts Service, Columbus, Ohio, US; Suetsugu, Maseru et al, "Skin conditioners containing lysine derivatives," retrieved from STN, Database accession No. 132:339047 HCA, XP002205557.
Database WPI Week 200033, Derwent Publications Ltd., London, GB; AN 2000-382026, XP002208222 & JP 2000 128726 A (Shiseido Co. Ltd.), May 9, 2000, Zusammenfassung.
Database WPI, Section Ch, Week 200057, Derwent Publications Ltd., London, GB; Class B07, AN 2000-602052, XP002208223—& WO 00 54750 A (Starchenko D A); Sep. 21, 2000, Zusammenfassung.
Database Biosis Online, Biosciences Information Service, Philadelphia, PA, US; 1992 Palmieri G., et al., "Clinical and Immunological Effects of a Lysine Arginine Association in Atopic Dermatitis," Database accession No. PREV199293081020, XP002205558, Zusammenfassung.
Himmi, E. H., et al., "Regulatory role of a peptide from the second constant domain of immunoglobulin G—II. In vitro effect on granuloma formation around *S. mansoni* eggs," Int. J. Immunopharmac. 1985; 7(2): 231-237.
Patent Abstracts of Japan, vol. 1998, No. 01; Jan. 30, 1998 & JP 09 249535 A (Honen Corp.), Sep. 22, 1997, Zusammenfassung.
Database CA Online, Chemical Abstracts Service, Columbus, Ohio, US; Terai, M., "Antibacterial, low-irritation cosmetics," retrieved from STN, Database accession No. 127:336470 HCA, XP002236549, Zusammenfassung.
Database WPI, Week 199802, Derwent Publications Ltd., London, GB; AN 1998-011903, XP002236550 & JP 09 255518 A (Noevir KK), Sep. 30, 1997, Zusammenfassung. Patent Abstracts of Japan, vol. 1998, No. 01, Jan. 30, 1998, & JP 09 255518 A (Noevir Co Ltd), Sep. 30, 1997, Zusammenfassung. .
Hiltz, M. E., et al., "Anti-Inflammatory Activity of α-MSH (11-13) Analogs: Influence of Alteration in Stereochemistry," Peptides 1991; 12: 767-771.
Macaluso, A., et al., "Antiinflammatory Influences of α-MSH Molecules: Central Neurogenic and Peripheral Actions," J Neurosci 1994;14(4): 2377-2382.
Richards, D. B., et al., "Effect of α-MSH 11-13 (Lysine-Proline-Valine) on Fever in the Rabbit," Peptides 1984; 5: 815-817.
Beers, M.H., et al., "The Merck Manual of Diagnosis and Therapy," 1999, Merck Research Laboratories, Whitehouse Station, NJ, XP002208945.
Thews, G., et al., "Anatomie, Physiologie und Pathophysiologie des Menschen," 1991, WVG, Stuttgart XP002236548.
Vuitton, D., "The ambiguous role of immunity in echinococcosis: protection of the host or of the parasite?" Acta Tropica 2003; 85: 119-132.

(Continued)

*Primary Examiner* — Cecilia Tsang
*Assistant Examiner* — Thomas Heard
(74) *Attorney, Agent, or Firm* — Dobe Law Group, LLC; Christopher Aniedobe

(57) ABSTRACT

The present invention relates to the use of a compound of the formula Lys-X where X is a hydroxyl group, an amino group, alkoxy, Pro or Pro-Thr, or of a pharmaceutically acceptable salt thereof, for the treatment of inflammations. The invention also relates to the use of αMSH for inducing tolerance.

4 Claims, 21 Drawing Sheets

OTHER PUBLICATIONS

International Search Report for PCT Application No. PCT/EP02/01323 prepared by the European Patent Office, issued on Apr. 29, 2003.

Klement et al. *IκBα Deficiency Results in a Sustained NF-κB Response and Severe Widespread Dermatitis in Mice*, Molecular and Cellular Biology, May 1996, p. 2341-2349.

Kwon et al. *Insulin-like Growth Factor II Induces Interluekin-6 Expression via NF-κB Activation in Psoriasis*, Biochemical and Biophysical Research Communications 278, 312-317 (2000).

Chen et al. *RAG2-/-, IκBα Chimeras Display a Psoriasisform Skin Disease*, J. Invest Dermatol 115:1124-1133, 2000.

Schmidt K.N. *Anti-Psoriatic Drug Anthralin Activates Transcripton Factor NFκB in Murine Keratinocytes*, The Journal of Immunology, 1996, 156:4514-4519.

Robert et al. *Inflammatory Skin Diseases, T-Cells, and Immune Surveilance*, The New England Journal of Medicine 341(24), 1817-1828, 1999.

Wirtz S, Neufert C, Weigmann B and Neurath F; Chemically Induced Mouse Models of Intestinal Inflammation. Nature Protocols vol. 2 No. 3. 2007 541-546.

Elson C.O, Sartor R.B., Tennyson G.S. and Riddel R H.; Experimental Models of Inflammatory Bowel Disease. Gastroenterology 1995:109:1344-1367.

\* cited by examiner

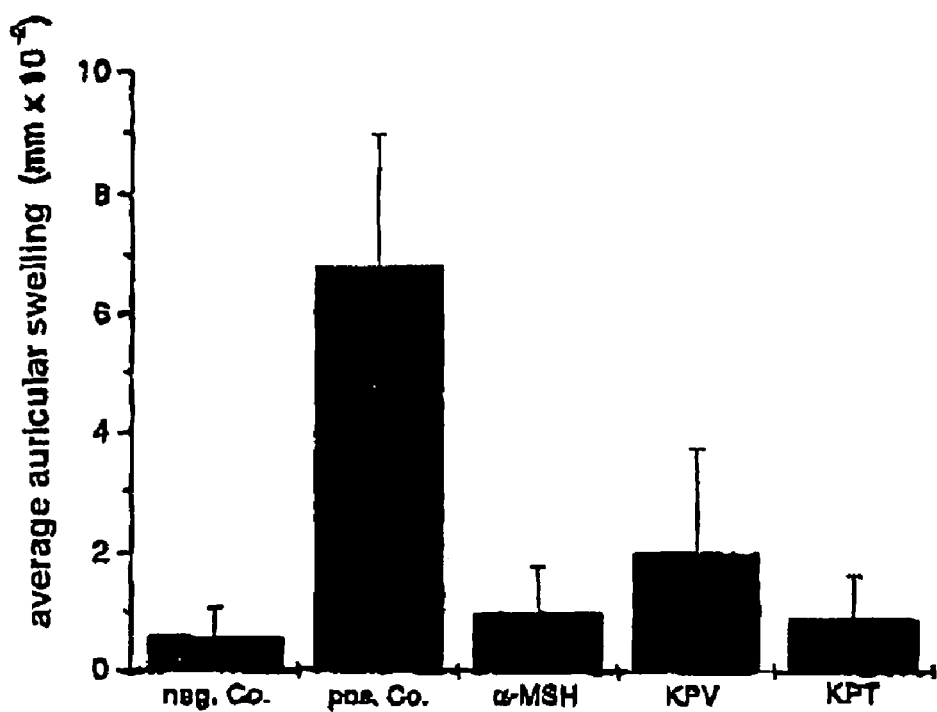
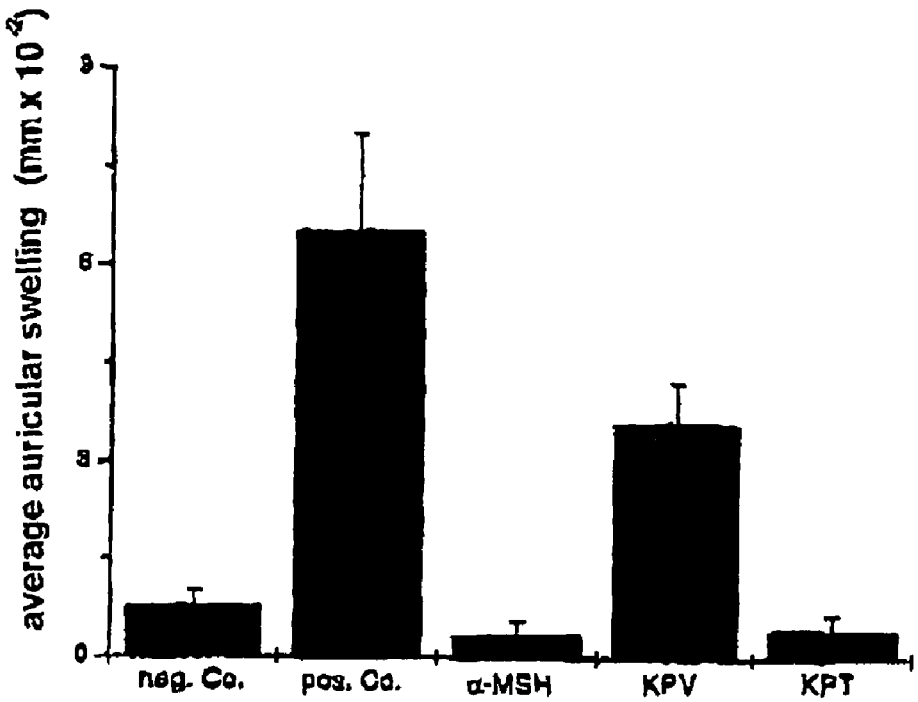
Fig. 2: Tolerance by αMSH and derived peptides

Fig. 10
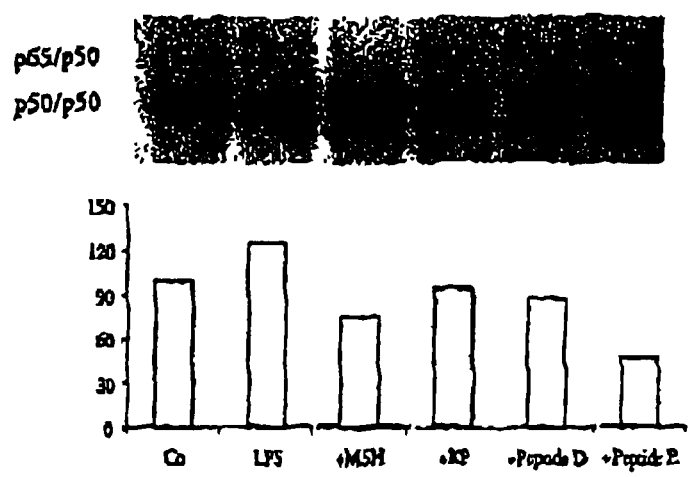
Fig. 11a
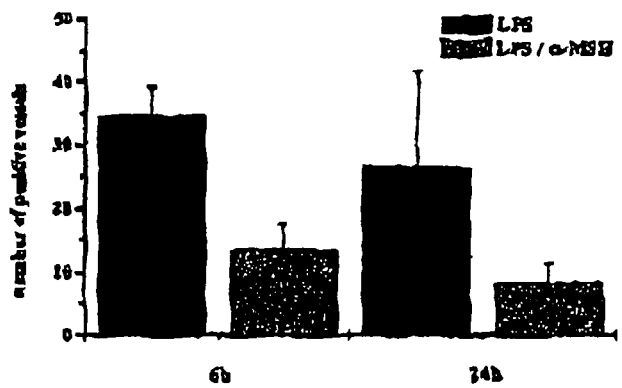
Fig. 11b
|  | 2 h | 3 h | 4.5 h |
|---|---|---|---|
| Pos. Co. (only LPS) | 6<br>3<br>5<br>6<br>5<br>3 | 10<br>6<br>5<br>15<br>10<br>3 | 10<br>6<br>6<br>15<br>15<br>6 |
| α-MSH | 0<br>15<br>1<br>0<br>0<br>0 | 0<br>20<br>1 + 6 small<br>0<br>0<br>0 | 0<br>20<br>1 + 6 small<br>0<br>0<br>0 |

Fig. 12
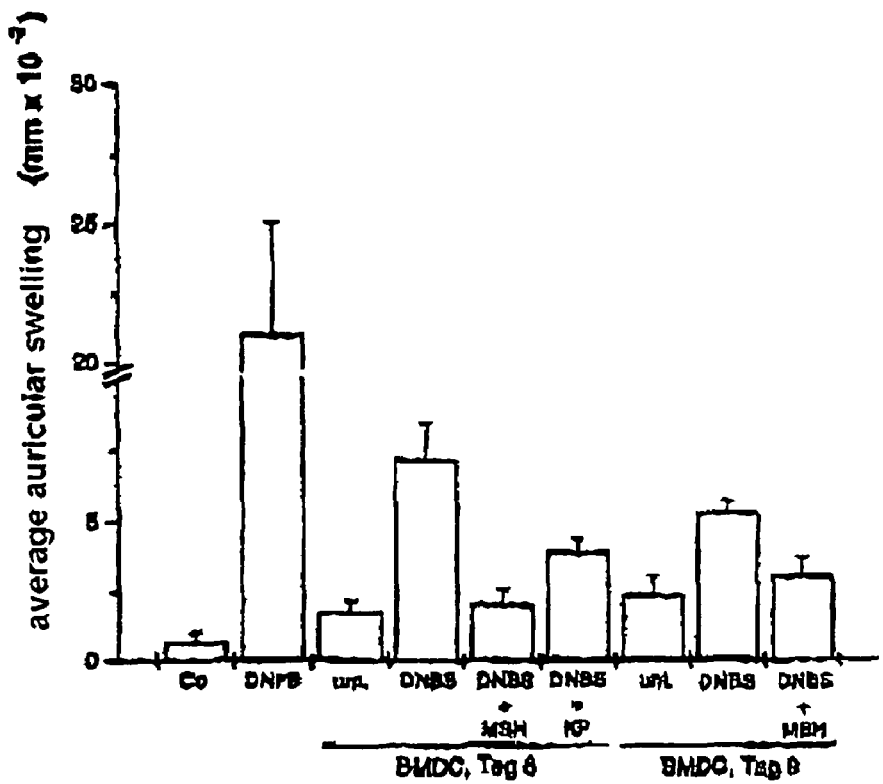
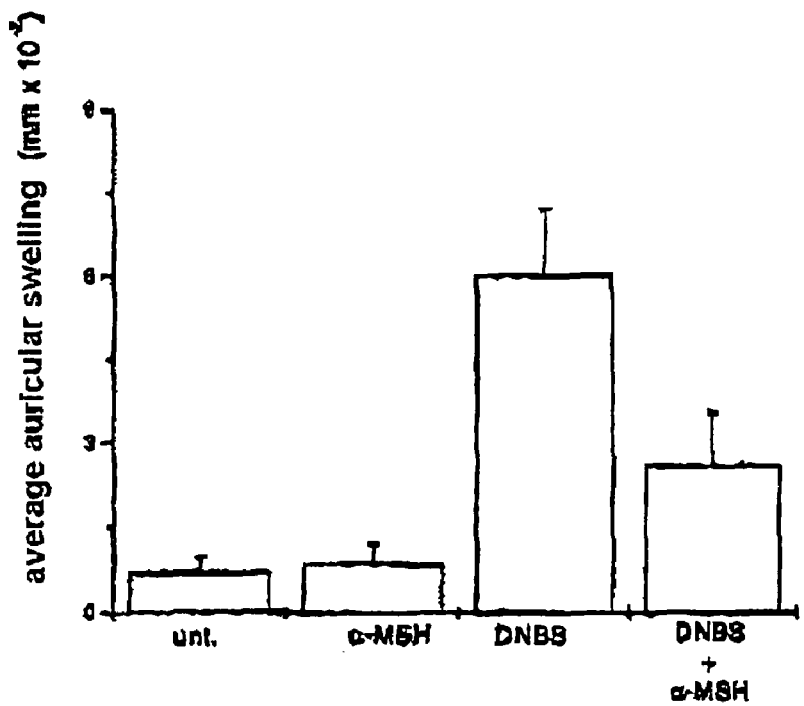

Fig. 13a
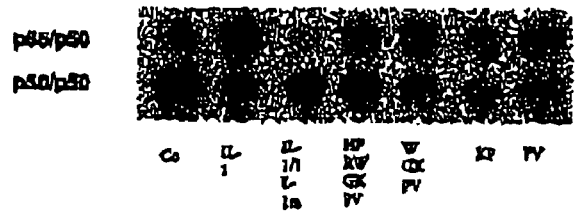
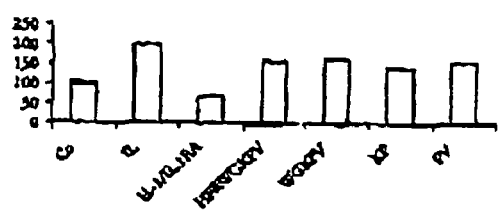
Fig. 13b
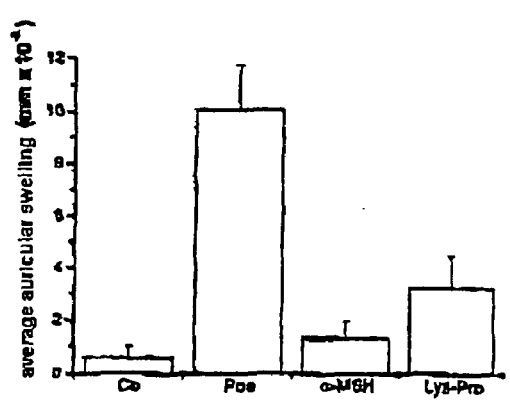
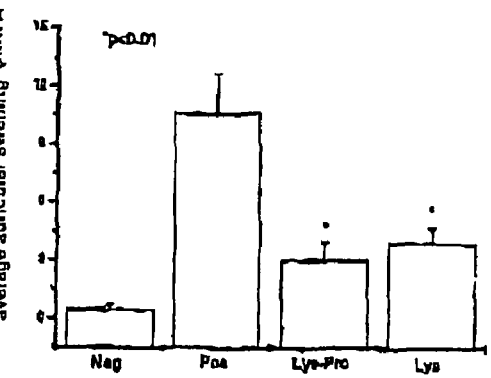
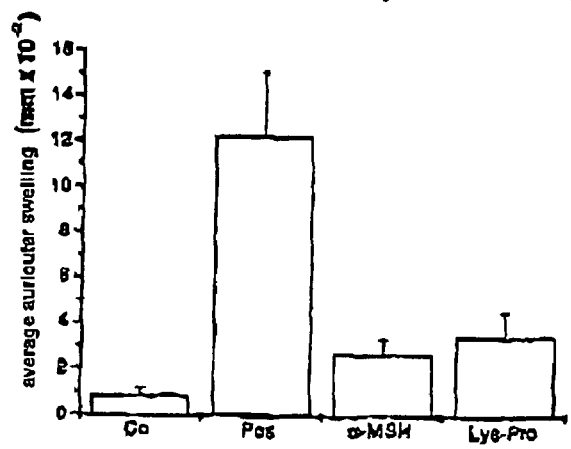

Fig. 16
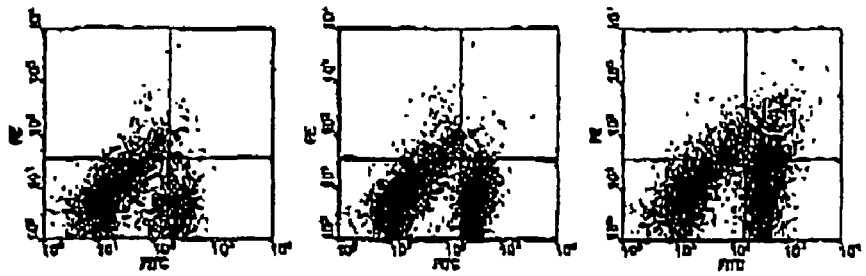
Co.    DNBS    DNBS + α-MSH
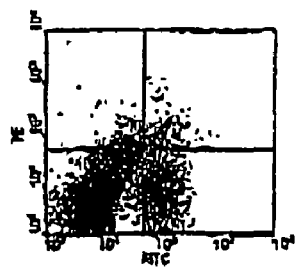 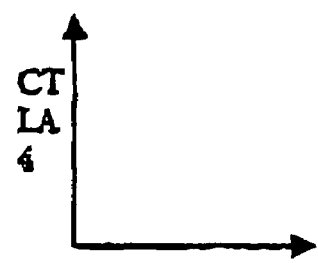
DNBS + KPV    DNBS + KPT
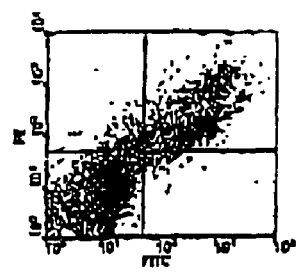 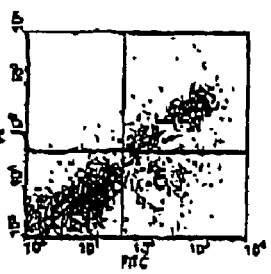
Co.    DNBS    DNBS + α-MSH
DNBS + KPV    DNBS + KPT

INFLAMMATION-INHIBITING COMPOUNDS

The tridecapeptide α-melanocyte-stimulating hormone (αMSH) is produced from the precursor hormone pro-opiomelanocortin (POMC). Several biologically active peptide hormones such as, for example, β-lipotropin, adrenocorticotropin (ACTH), β-endorphin and the melanotropins (α-, β- and γMSH) are derived from the POMC gene product. Proteolytic enzymes with various specificities are necessary for processing these peptides. In addition, post-translational modifications such as acetylations may take place.

The effects of αMSH and other POMC peptides on the various tissues are mediated by a family of specific receptors. These melanocortin (MC) receptors belong to the group of G protein-coupled receptors. Five different melanocortin receptors (MC-1 to MC-5) have been cloned. It is assumed that αMSH is an important signal for regulating various melanocyte functions. It is thought, for example, that proliferation, differentiation and cytokine production by melanocytes are influenced by αMSH.

It has also been shown that POMC gene products are able to influence immune responses and inflammatory reactions. For example, it is assumed that αMSH down-regulates several proinflammatory cytokines, while the production of the antiinflammatory cytokine IL-10 is stimulated by αMSH. This means that αMSH has an important function in the suppression of immune responses and inflammatory reactions. Several studies indicate that the immunomodulatory and antiinflammatory effects of αMSH are mediated by the C-terminal region of αMSH (amino acids 11-13: Lys-Pro-Val) because administration of the C-terminal tripeptide is sufficient to induce these effects (Catania and Lipton, 1993, Endocr. Rev. 14, 564-576; Bhardvaj et al., 1996, J. Immunol. 156, 2517-2521).

WO 88/00833 discloses the use of the tripeptide Lys-Pro-Val for producing a medicament for the treatment of inflammations. The C-terminal tripeptide of αMSH has likewise been proposed as agent to prevent loss of hair (FR 2 733 421).

One object of the present invention is to provide further inflammation-inhibiting compounds.

It has surprisingly been found that the tripeptide Lys-Pro-Thr has antiinflammatory properties. Unexpectedly, even smaller compounds such as Lys-Pro and Lys also show advantageous properties.

The present invention therefore relates to the use of a compound of the formula (I)

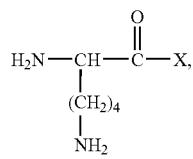

(I)

where X is a hydroxyl group, an amino group, alkoxy, Pro or Pro-Thr, or of a pharmaceutically acceptable salt thereof, for the treatment and/or prevention of inflammatory disorders. The term "inflammatory disorders encompasses not only inflammations but also disorders in which an inflammation is involved, such as, for example, autoimmune diseases or transplant rejections.

The compound used according to the invention may be lysine or the dipeptide lysine-proline, but the tripeptide lysine-proline-threonine (=KPT) is preferably used.

Naturally occurring amino acids usually have the (L) configuration. The amino acids of the compounds used according to the invention may have either the (L) or the (D) configuration. Possible compounds of the KPT structure are thus (L)Lys-(D)Pro-(L)Thr,
(L)Lys-(L)Pro-(D)Thr,
(L)Lys-(D)Pro-(D)Thr,
(L)Lys-(L)Pro-(L)Thr,
(D)Lys-(D)Pro-(L)Thr,
(D)Lys-(D)Pro-(D)Thr,
(D)Lys-(L)Pro-(L)Thr,
(D)Lys-(L)Pro-(D)Thr, with the compound (L)Lys-(D)Pro-(L)Thr being most preferred. The compounds used according to the invention may also show amino acid exchanges, with one of the amino acids having been conservatively changed.

The compound of the formula (I) used according to the invention may be chemically modified at the N terminus and/or at the C terminus, for example by an acyl group, preferably an acetyl group at the N terminus and/or an amidation or esterification of the C terminus. Further protective groups known per se are likewise possible. The modifications may also affect the amino group in the side chain of lysine or the hydroxyl group of threonine. Other modifications are also conceivable on the side of the $NH_2$ group, e.g. extension by a glycine, and further amino acid residues up to the length of α-MSH.

For the purposes of the present application, the term "compound of the formula (I)" also includes the pharmaceutically acceptable salts of the compound.

Said compounds can be used for the treatment of all types of acute or chronic inflammations. These include inter alia acute and chronic inflammations for example of the skin, psoriasis, atopic dermatitis, allergic reactions of all types, from rhinitis via contact allergies to asthma and food allergies, autoimmune diseases, fibroses and sclerodermas and transplant rejection but also vascular disorders. The compounds are preferably used for the treatment of inflammatory conditions of the skin. It is advantageous in this case to administer the compound as topical formulation in the form of an ointment or cream. The compound is normally present in an ointment or cream in a concentration of from 1 μM to 1 mM, preferably from 10 μM to 100 μM. Such an ointment or cream may additionally comprise conventional ingredients as described, for example, in Braun-Falco et al. (1996) Dermatologie und Venerologie, Springer Verlag, Berlin or Merk, Bickers (1992) Dermatopharmakologie und Dermatotherapie.

It is possible in a preferred embodiment for the peptides also to be used according to the invention for inflammatory bowel disorders. Examples of inflammatory disorders are, besides short-term irritations of the bowel caused by relatively mild food poisonings, also chronic bowel disorders such as Crohn's disease or ulcerative colitis.

In another preferred embodiment, the compounds can be used according to the invention for the treatment of inflammatory disorders of inflammations occurring at sites in the body which come into contact with the environment. These include in particular the mucous membrane of the mouth and gastrointestinal tract, and of the lung.

The compounds used according to the invention do, however, also have systemic activity for the treatment or prevention of inflammations. The compound is then preferably administered intraperitoneally, intravenously or orally. The dose of an administration is usually 20 μg to 10 mg/kg of body weight, preferably 100 μg to 1 mg/kg of body weight.

Finally, said compounds can also be used in sprays, for example for inhalation for the treatment of inflammations of the airways.

It is possible to employ a plurality of different compounds of the formula (I) for the treatment. In this embodiment, at least two different compounds of the formula (I) are used for the treatment of inflammations.

The compounds of the formula (I) can also be used to produce a medicament for the treatment and/or prevention of inflammations. All the embodiments indicated above are encompassed analogously by this use. The compound is normally mixed with a pharmaceutically acceptable carrier or diluent. Processes known per se for producing medicaments are indicated in Forth, Henschler, Rummel (1996) Allgemeine und spezielle Pharmakologie und Toxikologie, Urban & Fischer.

The compounds of the formula (I) may also be added to foods in order to reduce the allergic potential of certain food constituents. The invention therefore also relates to the use of a compound of the formula (I) as addition to foods. The concentration in foods may then be 1 µM to 1 mM.

It is also possible according to the invention to use a compound of the formula (I) as non-pharmaceutical addition in cosmetics. For example, creams comprising a compound of the formula (I) can be employed for irritated skin or after sunbathing.

Surprisingly, the inventors have likewise found that treatment of dendritic cells in vitro with a hapten and αMSH and subsequent injection of the cells into experimental animals leads to the production of hapten-specific tolerance and to suppression of the CHS reaction ("contact hypersensitivity reaction"). The present invention therefore further relates to a method for the in vitro production of cells able to confer tolerance to an antigen, which comprises provision of antigen-presenting cells, bringing the cells into contact with αMSH or a biologically active derivative or fragment thereof, and bringing the cells into contact with the antigen, where the last two steps can be carried out in any sequence or simultaneously.

There are various types of antigen-presenting cells. Dendritic cells or Langerhans cells are preferred according to the present invention. It is unnecessary for the antigen-presenting cells to be present in a preparation which is free of other constituents or cells. The antigen-presenting cells can also be provided mixed with other cells. A preferred example is the provision of epidermal cells in which Langerhans cells are present as antigen-presenting cells. It is also possible to isolate dendritic cells from bone marrow or produce dendritic cells from precursor cells such as, for example, PBMC by in vitro culture known per se. Methods for providing antigen-presenting cells are described for example in Labeur et al. J. of Immunol. 162(1):168-175 (1999).

The cells are then brought into contact in vitro with αMSH or a biologically active derivative or fragment thereof. Biologically active derivatives or fragments of αMSH are, for example, chemical modifications of αMSH, fragments of αMSH including Lys, Lys-Pro, Lys-Pro-Val or Lys-Pro-Thr, or compounds comprising one of said substances. A wide variety of modifications is conceivable as long as the biological activity of αMSH—the ability to induce tolerance—is substantially retained. Normal concentrations of αMSH or said derivatives on being brought into contact with the cells are $10^{-6}$ M to $10^{-16}$ M, preferably $10^{-8}$ M to $10^{-12}$ M.

After the cells have been brought into contact with αMSH or a biologically active derivative or fragment thereof, or previously or simultaneously, the cells are brought into contact in vitro with the antigen against which tolerance is to be induced. The antigen may in this case be a protein against which there is the risk of an allergic reaction. If, for example, it is known against which hapten of the antigen the immune response is directed, the cells can also be brought into contact only with the specific hapten. Possible examples in this connection are peptides with a length of from 7 to 20 amino acids, preferably from 7 to 15 amino acids.

The antigen-presenting cells can be washed after said steps and be mixed with a pharmaceutically acceptable or carrier or diluent. The cells can then be introduced into a patient or into a mammal, whereupon tolerance is produced against the hapten or antigen used.

A further aspect of the invention is the use of αMSH or of a biologically active derivative or fragment thereof for producing a medicament for inducing tolerance to an antigen. The produced medicament preferably comprises cells which are obtainable by the method described above for the in vitro production of cells able to confer tolerance.

The peptide Lys-Pro-Thr prevents the activation of the transcription factor NF-κB by TNFα, IL-1 or LPS in endothelial cells and in keratinocytes. The consequence is a reduced expression of cell adhesion molecules (endothelial cells) and chemokines (keratinocytes). The inventors have also been able to show that, for example, the KPT peptide prevents the occurrence of contact allergies (contact hypersensitivity reactions, CHS reactions) and induces an allergen-specific, long-lasting tolerance. Two sections are to be distinguished in CHS reactions: initial contact (induction phase) with an antigen lays the foundation for the later CHS reaction, and a further contact with the antigen leads to the occurrence of the reaction (contact dermatitis, i.e. swelling, itching, etc.). The compounds used according to the invention can be employed before both sections, and when employed (injection or topical application) before the initial contact there is suppression of the CHS and induction of tolerance, and when employed at the time of induction of the contact dermatitis the compounds prevent the occurrence of the dermatitis. In all these applications there is substantially complete inhibition of the allergic reaction.

It has likewise been found that Lys-Pro-Thr reduces the expression of costimulatory molecules on dendritic cells. This is most likely part of the mechanism associated with the suppression of the CHS and the induction of tolerance. At the same time, the compounds increase the secretion of the anti-inflammatory IL-10 by monocytes. This effect is likewise part of the mechanism associated with the allergic contact dermatitis.

Without wishing to be bound in any way to one theory, the compounds of the invention might bind to β-adrenergic receptors. It can additionally be assumed that the peptides employed according to the invention are capable of binding to the type I IL-1 receptor. Nor can it be precluded that the peptides of the invention also bind to other receptors such as, for example, the κ opioid receptor. Based on this assumption, it is presumed that the peptides of the invention are able to bind to a plurality of receptors which, after activation by their original ligands, would all intervene in a proinflammatory way in the inflammatory event. The binding of the peptide of the invention to these receptors prevents the binding of the original ligands to these receptors, and thus the induction of the proinflammatory effects is prevented. On the other hand, the binding of the peptides of the invention to the receptors of their initial substances (αMSH) activates these receptors and thus induces a further component of the mechanism of action, which is overall antiinflammatory.

FIG. 1 shows that intravenous injection of αMSH, KPV or KPT suppresses the CHS sensitization phase.

FIG. 2 shows that intravenous administration of αMSH, KPV or KPT is able to induce tolerance.

FIGS. 6a to d, 7a to d and 8a to d show that unlabeled αMSH, KPV or KPT are able to displace biotin-labeled αMSH from binding sites on THP-1 cells in a competitive assay.

Figure 9A:
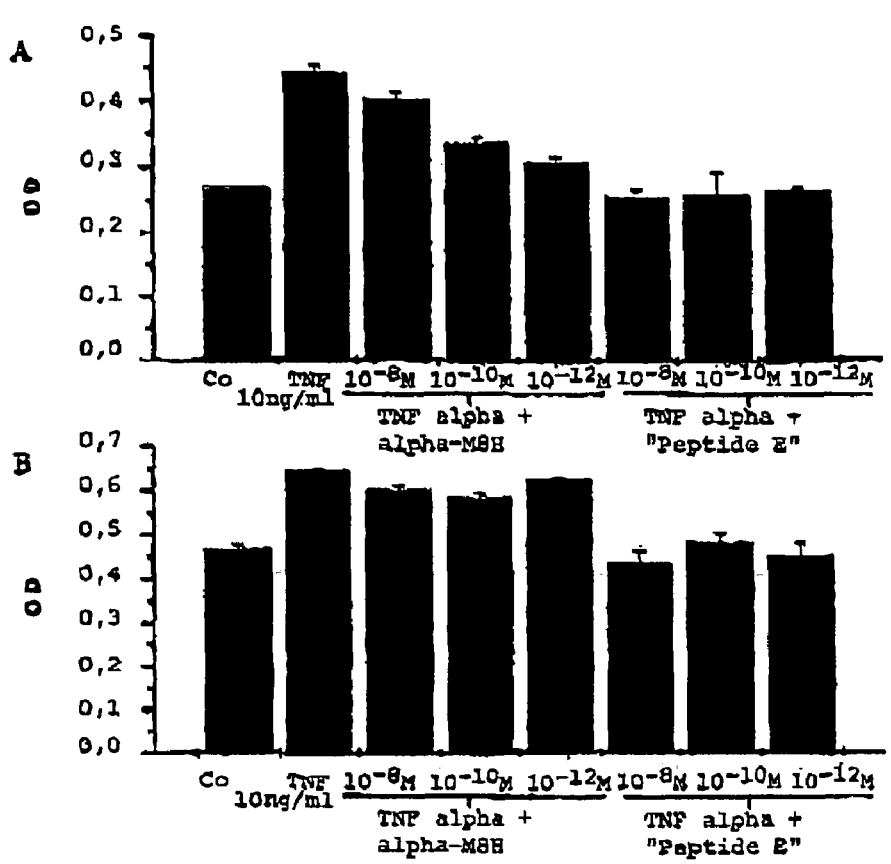

FIG. 9a shows the expression of cell adhesion molecules (CANS) on the surface of HMEC-1 cells 24 hours after treatment by TNFα+αMSH or TNFα+KPT.

Figure 9B:
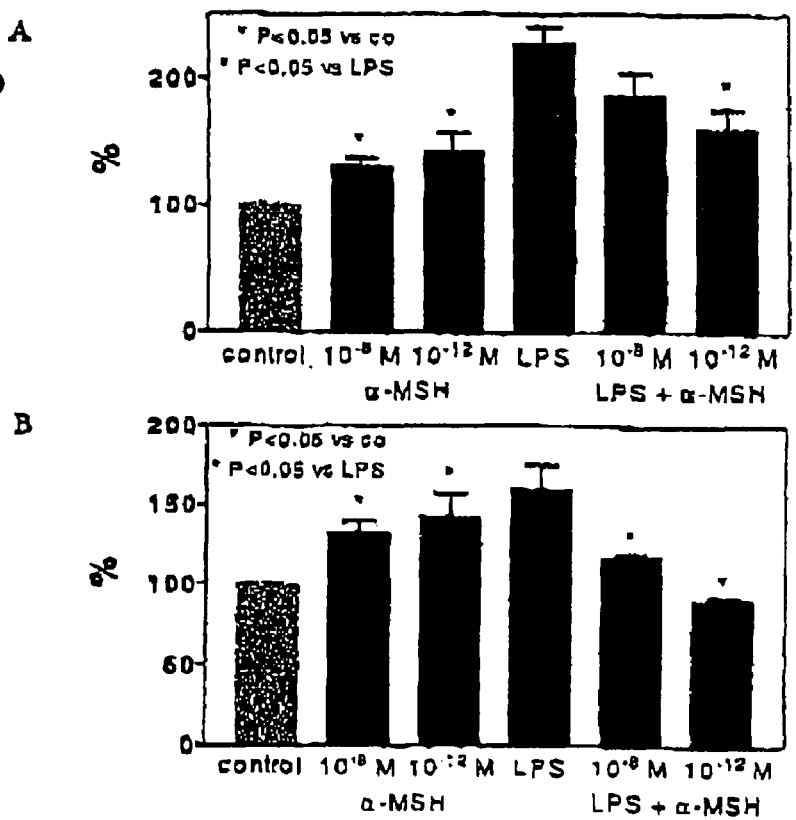

FIG. 9b shows the adhesion of lymphocytes to HDMEC (chromium release assay). A: molt4 T lymphocytes; B: JY B lymphocytes.

FIG. 10 shows the effect of αMSH, KP, KPV or KPT on NF-κB activation in LPS-treated HMEC-1 cells.

FIG. 11a shows that the number of E selectin-expressing vessels in tissue sections is reduced by αMSH treatment.

FIG. 11b shows that the number of petechial lesions on the ears of LPS-treated mice is reduced by αMSH treatment.

FIG. 12 shows that in vitro treatment of BMDC with αMSH or KP suppresses CHS and can induce tolerance.

FIG. 13a shows that in an NF-κB band shift assay the intensity of the NF-κB p65/p50 heterodimer band is reduced by various αMSH-derived peptides.

FIG. 13b shows the effect of αMSH, KP or K on the CHS reaction and the effect of αMSH or KP on the induction of tolerance in Ba1bC mice.

Figure 14:
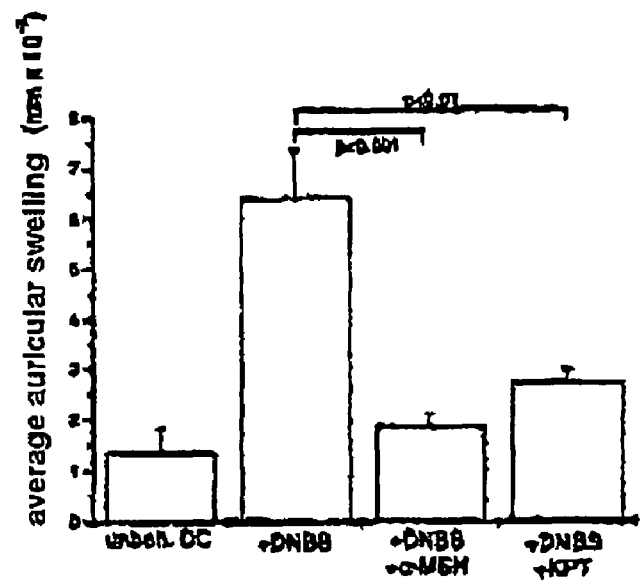

FIG. 14 shows the suppression of CHS by T cells which have been contacted in vitro with antigen-loaded and αMSH or derivative-treated DC.

Figure 15:
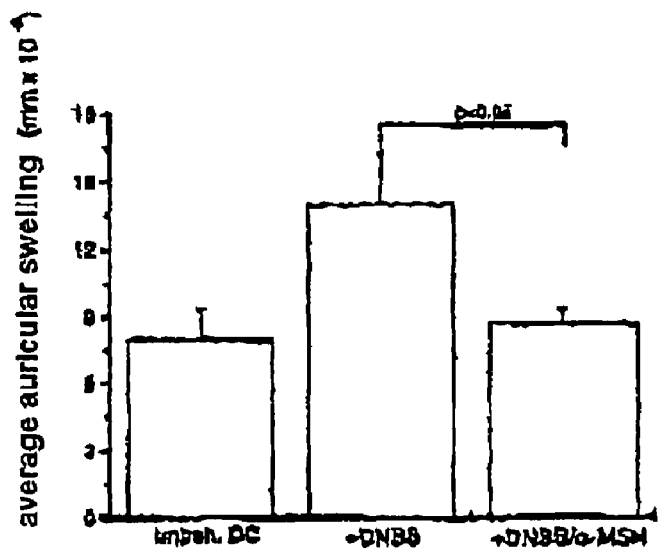

FIG. 15 shows the induction of tolerance by T cells which have been contacted in vitro with antigen-loaded and αMSH DC.

FIG. 16 shows the up-regulation of CTLA-4 on T cells after contact with antigen-loaded and αMSH or derivative-treated DC. A: CD4 positive T cells; B: CD8 positive T cells.

The following examples are intended to explain the invention in more detail.

EXAMPLE 1

Mice:

7 to 10 week old female Ba1b/C mice were obtained from Charles River (Sulzfeld, Germany) and kept in compliance with government regulations.

Administration of αMSH or KPV or KPT or KP:

αMSH and the peptides were stored as aliquots at −20° C. until used. Before the injection, the particular compound was dissolved in PBS, 0.1% mouse serum, and stored on ice until injected i.v. into the tail vein of the mice. 5 μg of αMSH or 1.5 μg of peptide (KP: 50 μg) per mouse were injected 2 hours before the sensitization.

Determination of CHS and Tolerance:

The mice were sensitized by spreading 75 μl of 0.5% DNFB in acetone/olive oil (4:1) on the shaven abdomen of naïve mice. CHS was induced by applying 10 μl of 0.3% DNFB to the ears of the mice on both sides of one ear. CHS was determined by the degree of auricular swelling of the hapten-exposed ear compared with the other, control-treated ear and was measured using spring-loaded dividers 24 hours after hapten exposure. Mice whose ears were exposed to hapten without previous sensitization served as negative controls. In order to determine whether the injection of αMSH or peptides before hapten administration leads to induction of tolerance, mice underwent i.v. injection (abdomen) or exposure (left ear) as described with αMSH or peptides 2 hours before the sensitization. To confirm the αMSH-induced suppression of CHS, mice were exposed to hapten on one ear 7 days after the sensitization, and the auricular swelling response was determined 24 to 36 hours later. 14 days later, the same mice were sensitized once again on the shaven back (now in the absence of exogenous αMSH), and investigated for their ability to induce a CHS response by a second exposure to hapten on the right ear one week later.

Topical preparations of αMSH were used in some experiments. In these experiments, application to the mice took place at the sensitization site (abdomen) immediately before or 3 hours or 24 hours before the sensitization.

Result:

I.v. injection of αMSH and of KPV or KPT or KP inhibits the ability of the mice to induce a CHS response to DNFB exposure taking place 7 days later. These mice thus developed no DNFB-specific sensitization. KPT suppressed the CHS response most effectively (see FIGS. 1 and 13b).

In order to distinguish between temporary immunosuppression and specific immunological tolerance, mice were sensitized a second time and exposed to hapten. Mice injected with αMSH or KPV or KPT before the first sensitization could not be sensitized even by administration of a second sensitizing dose of hapten, which indicates that these mice have developed tolerance to DNFB. KPV showed a weak effect, whereas αMSH and KPT and KP inhibited the auricular swelling response very greatly (see FIGS. 2 and 13b).

EXAMPLE 2

Material and Methods:

Mononuclear cells (PBMC) were separated from human buffy coats by Ficoll Hypaque density gradient centrifugation. Cells ($1\times10^6$ per ml), cultivated in RPMI 1640 with antibiotics and 10% FCS, were either not treated or stimulated with αMSH or the peptides KPV or KPT with or without IL-1β (10 U/ml) The supernatants of the PBMC cultures were collected after incubation for 24 or 48 hours and stored at −20° C. until used further. A commercially available ELISA was employed to detect IL-10.

Figure 3:
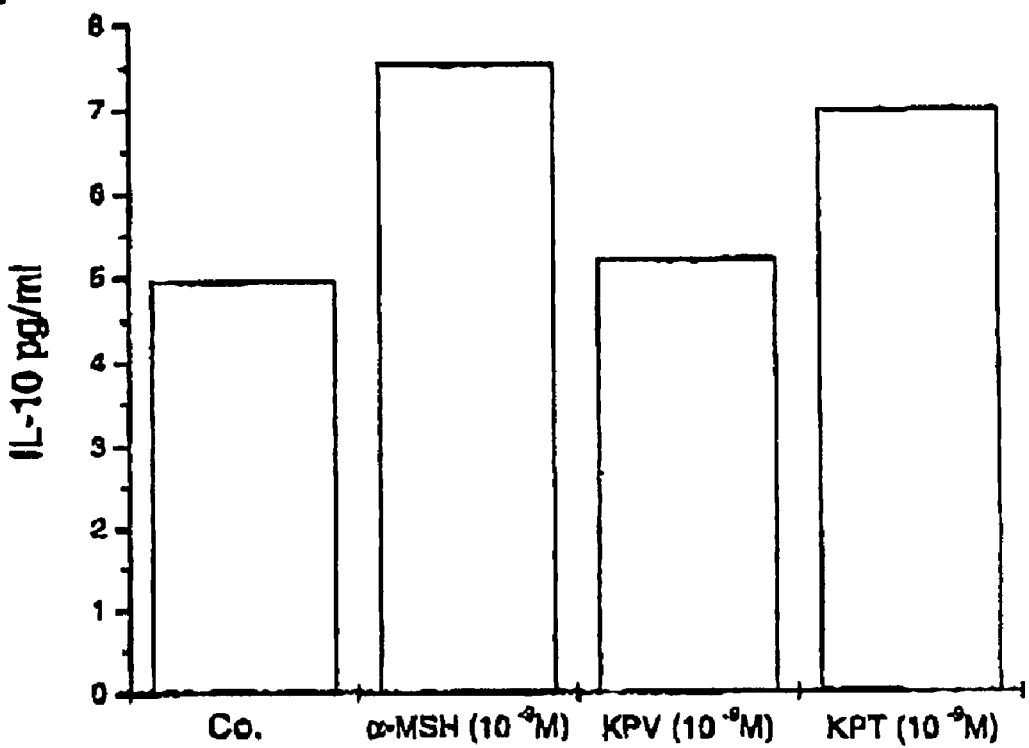
FIG. 3 illustrates IL-10 secretion by human PBL 24 hours after treatment with αMSH, KPV or KPT.

Results:

Human PBMC which were untreated or had been treated with various concentrations of αMSH or peptides produced only low concentrations of IL-10 (5-10 pg/ml) after incubation for 24 hours. αMSH ($10^{-11}$ M), KPV ($10^{-8}$ to $10^{-9}$ M) and KPT ($10^{-8}$ to $10^{-9}$ M) evidently induced IL-10 production (see FIG. 3).

Figure 4:
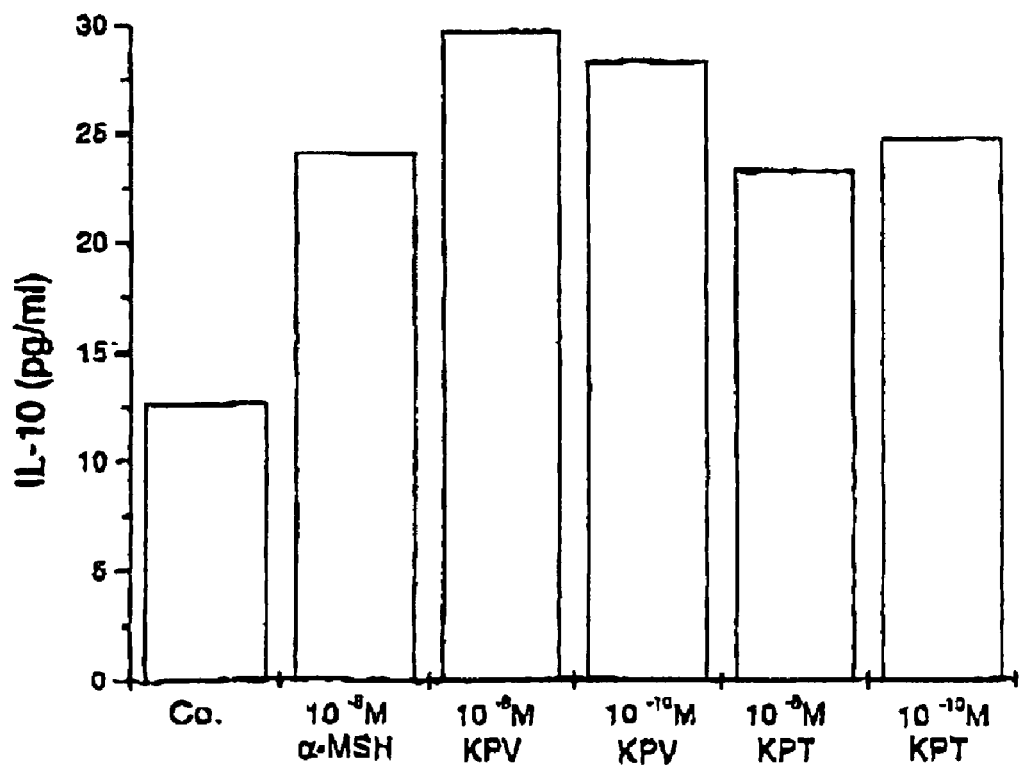
FIG. 4 illustrates IL-10 secretion by human PBL 48 hours after treatment with αMSH, KPV or KPT.

The human PBMC produced significant amounts of IL-10 after incubation for 48 hours. αMSH, KPV and KPT significantly increased the production of IL-10 by human PBLC. There was no essential difference between αMSH and the peptides (see FIG. 4).

The results which are shown prove that the peptide KPT is able, like αMSH and KPV, to inhibit the sensitization of CHS after intravenous administration and to induce hapten-specific tolerance. KPT is also able to induce IL-10 in vivo and in vitro. The data also make it probable that the immunosuppressant effect of αMSH in vivo depends not just on IL-10 induction.

EXAMPLE 3

Material and Methods:

All the steps were carried out at 0 to 4° C. The monocytic cell line THP-1 was washed once in PBS, once one acidic glycine buffer (50 mM glycine, 100 mM sodium chloride, pH 3) and three times with RPMI. The cells ($2.5 \times 10^6$ per ml) were then resuspended in 100 μl of RPMI/1% BSA and transferred into 96-well microtiter plates. After addition of biotin-labeled αMSH ($10^{-10}$ M), the cells were incubated at 4° C. for 1 hour, washed once with PBS, resuspended in 100 μl of PBS/1% BSA and incubated with FITC-labeled streptavidin (40 μg/ml) in the dark at 4° C. for 30 minutes. After a last washing step, the cells were resuspended in PBS. The amount of bound biotin-labeled αMSH was analysed using a flow cytometer. In control experiments, the cells were incubated without biotin-labeled αMSH but in the presence of FITC-streptavidin. Dead cells were excluded by adding propidium iodide shortly before the FACS analysis. The specificity of the binding of the biotin-labeled MSH was determined by adding unlabeled αMSH ($10^{-6}$ to $10^{-12}$ M) or KPV or KPT ($10^{-6}$ to $10^{-12}$ M).

Figure 5:
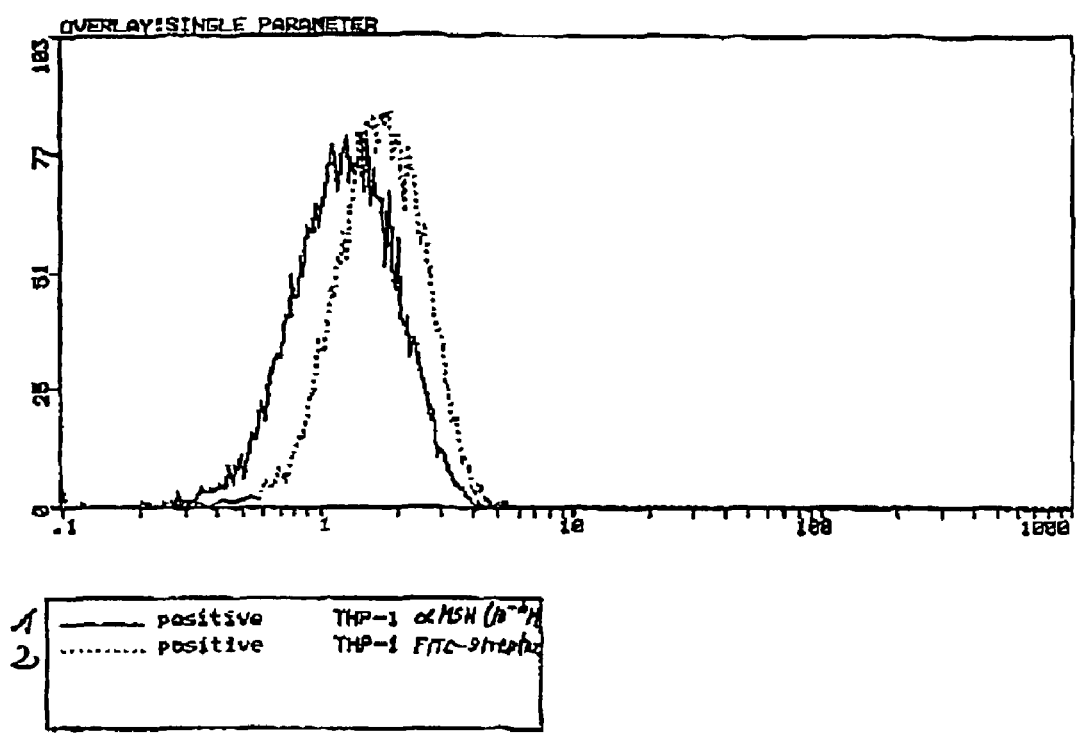
FIG. 5 shows that THP-1 cells express receptors for αMSH.
Figure 6A:
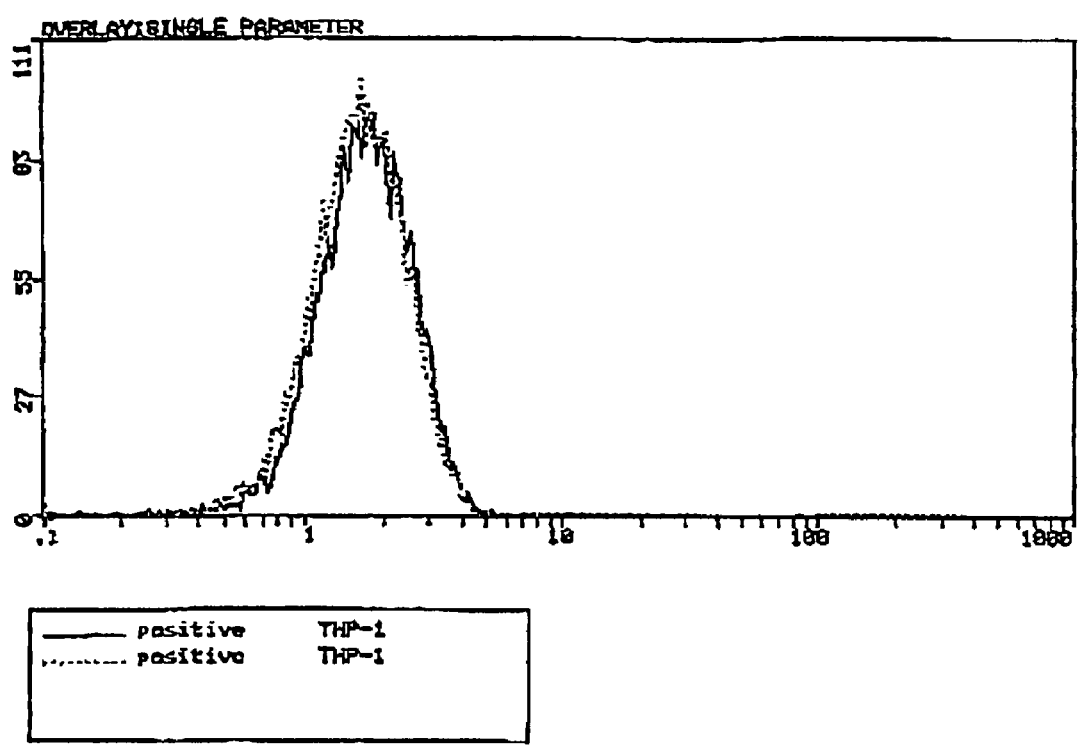
Figure 6B:
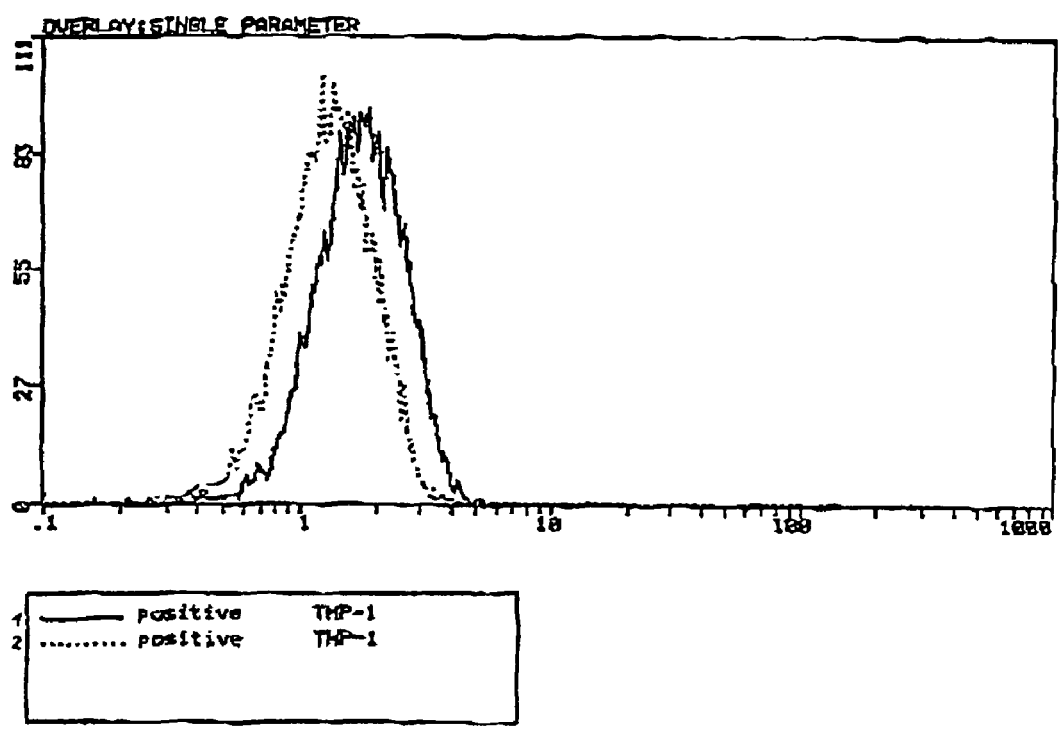
Figure 6C:
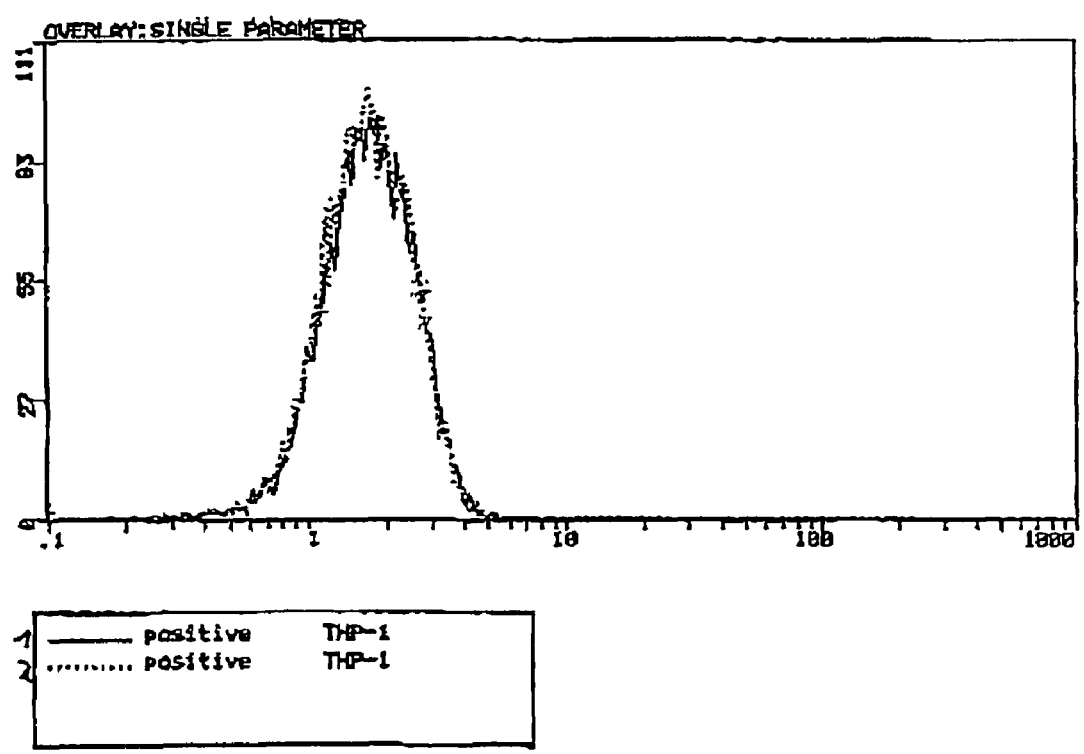
Figure 6D:
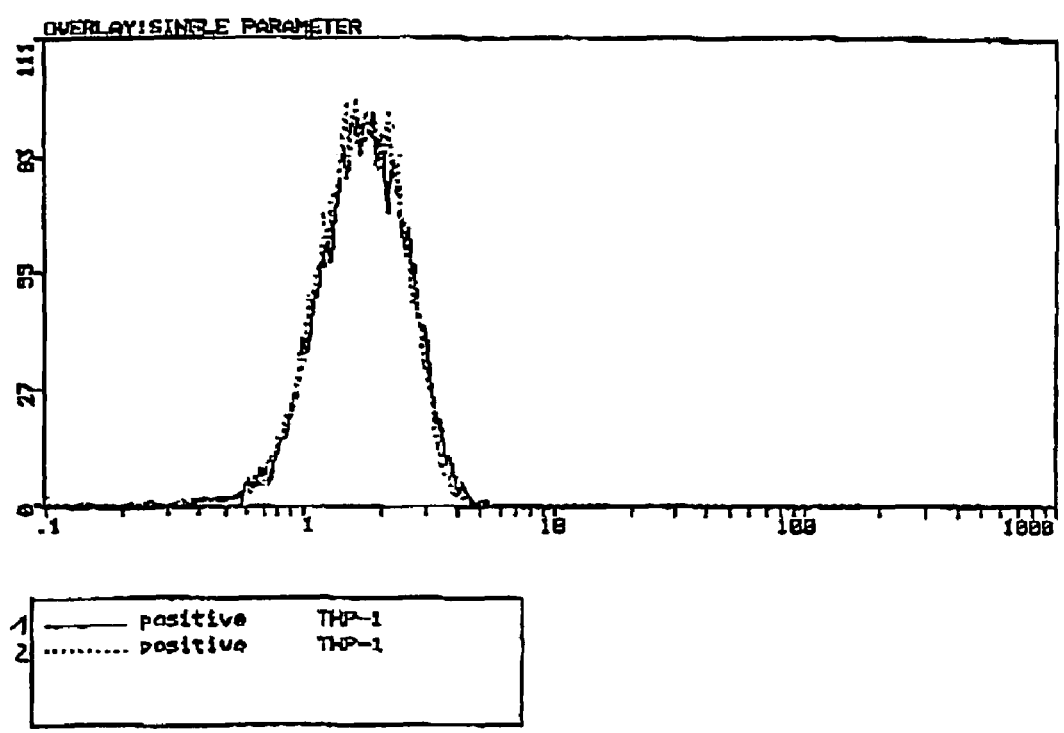
Figure 7A:
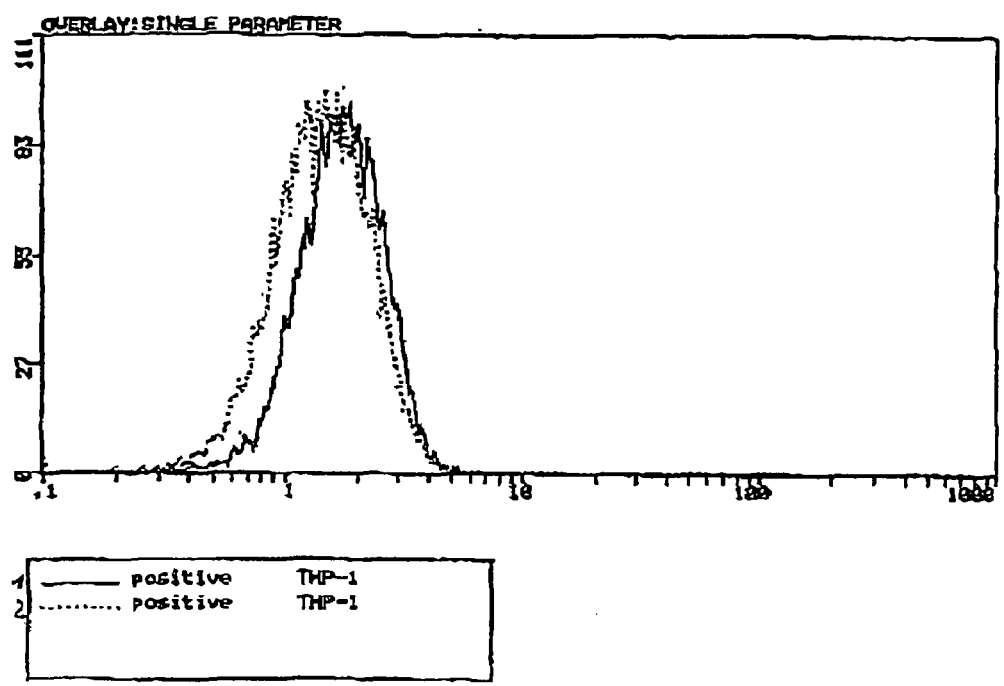
Figure 7B:
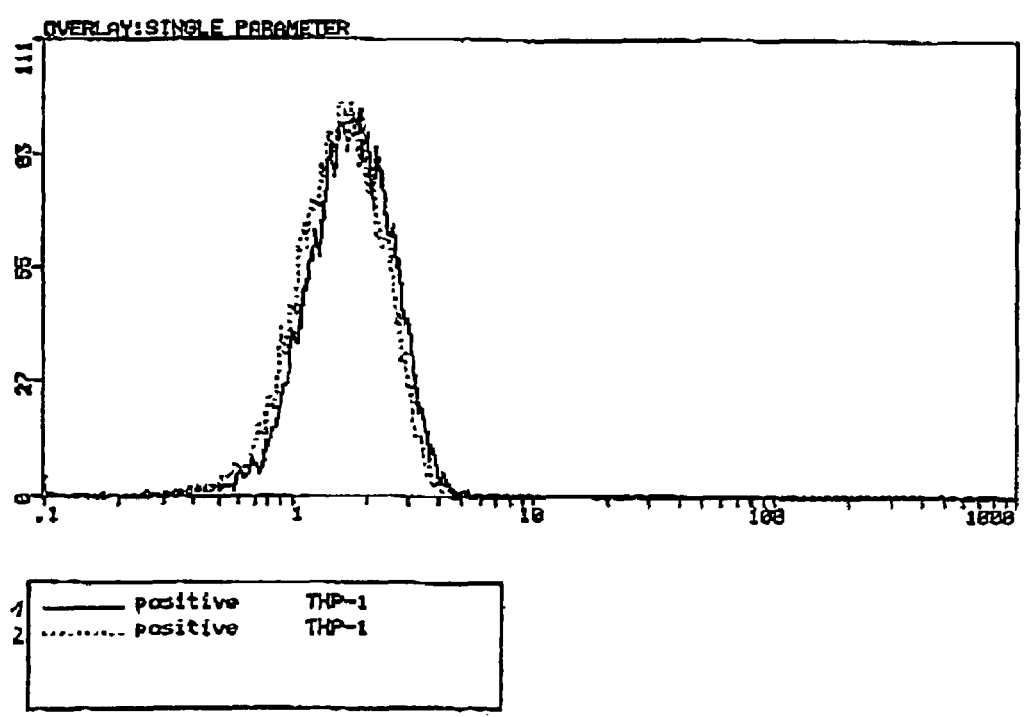
Figure 7C:
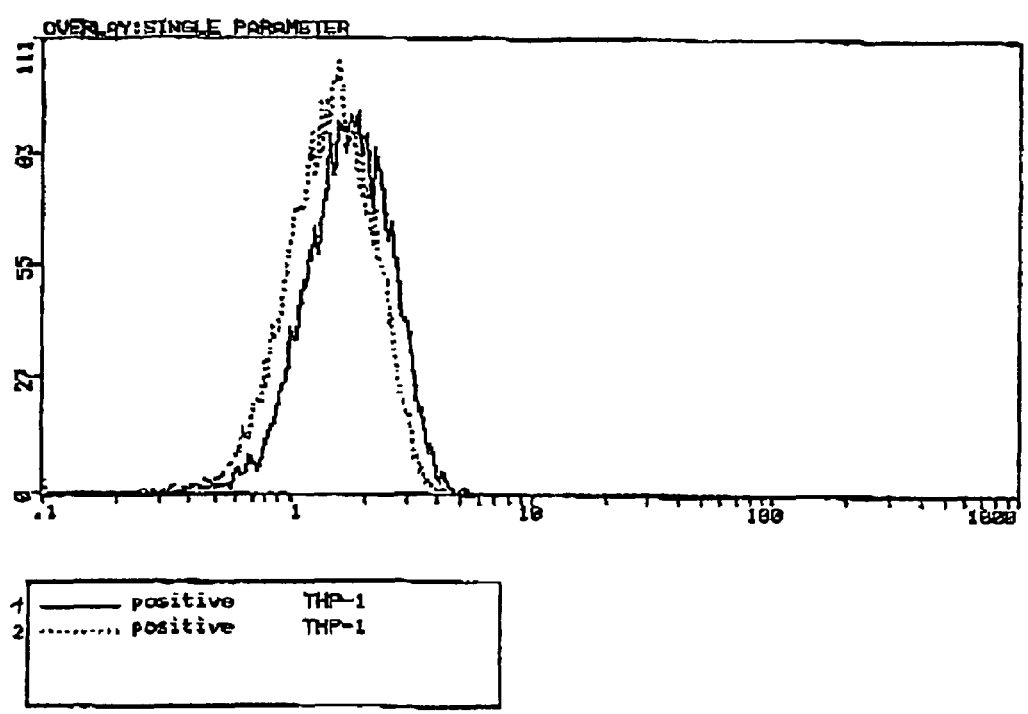
Figure 7D:
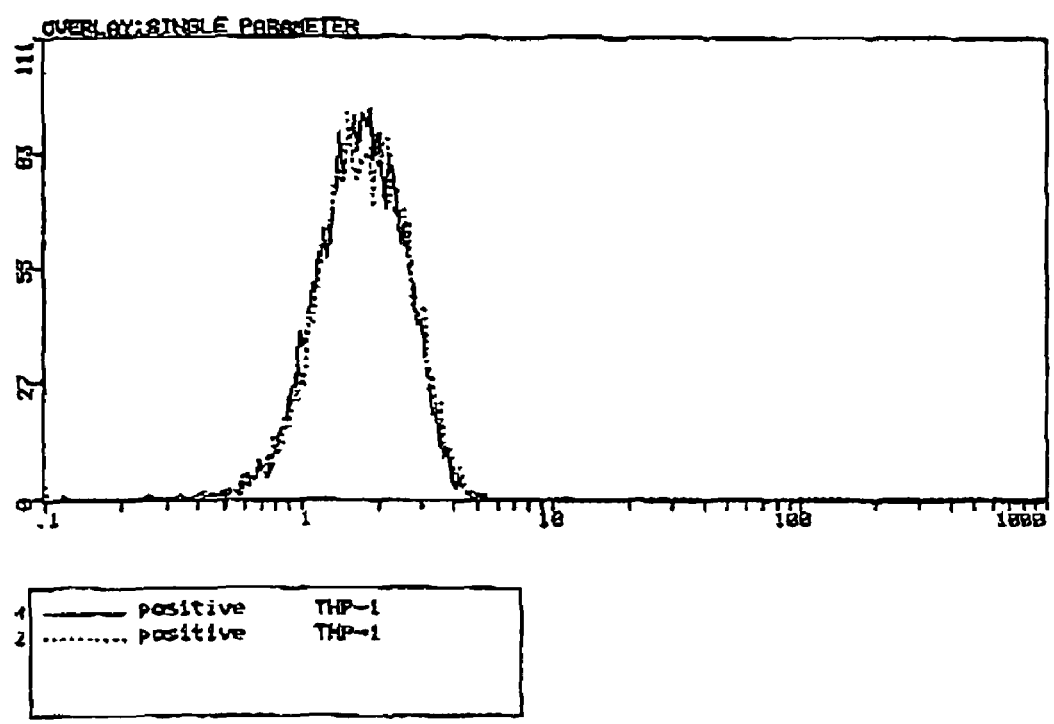
Figure 8A:
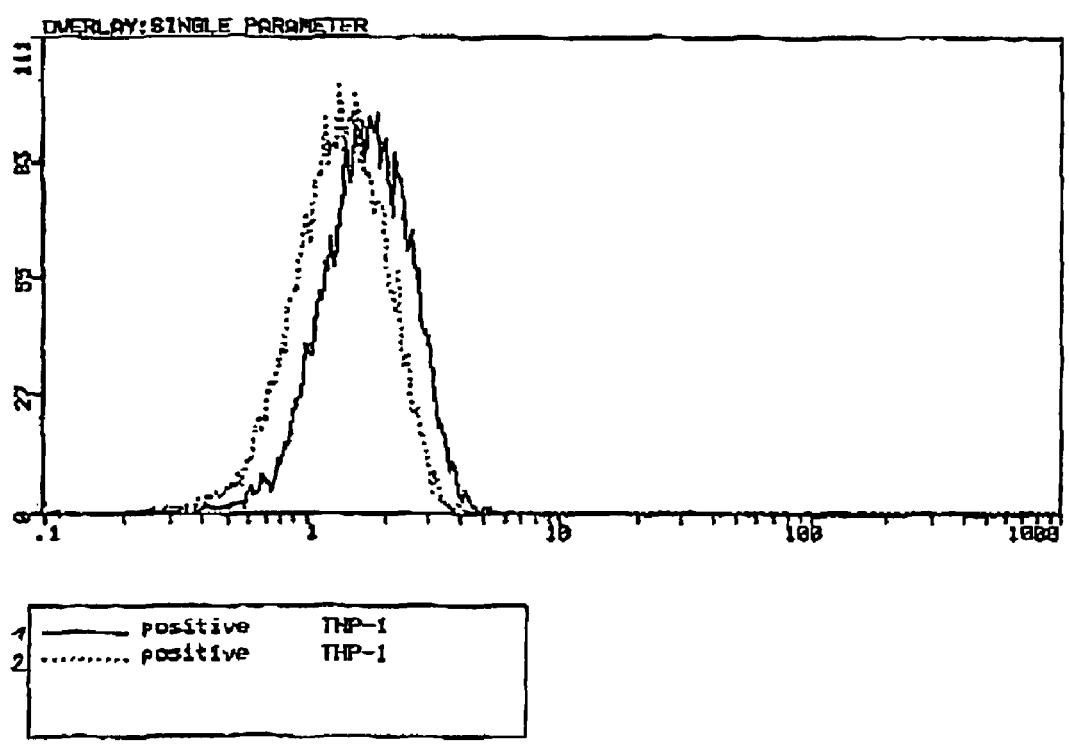
Figure 8B:
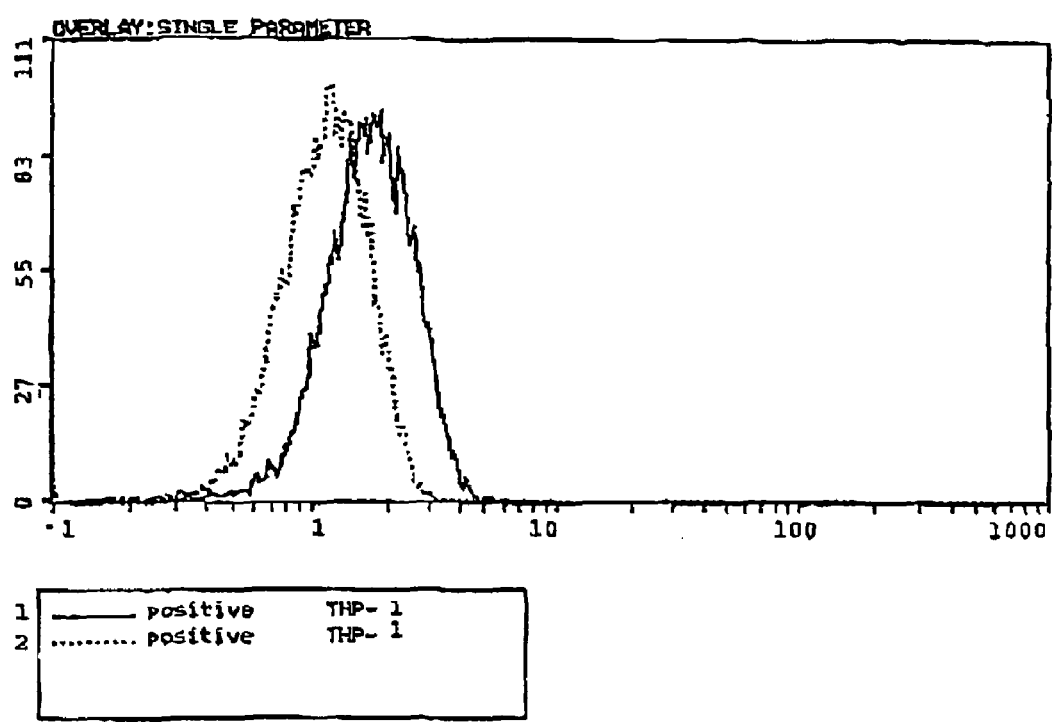
Figure 8C:
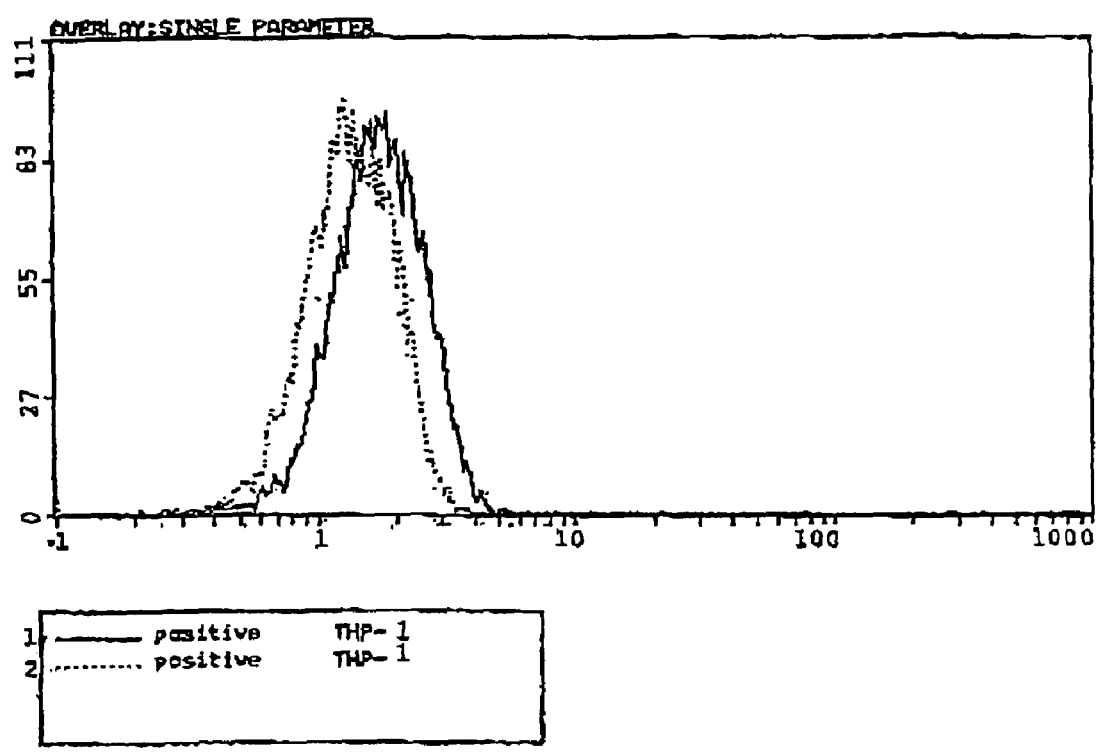
Figure 8D:
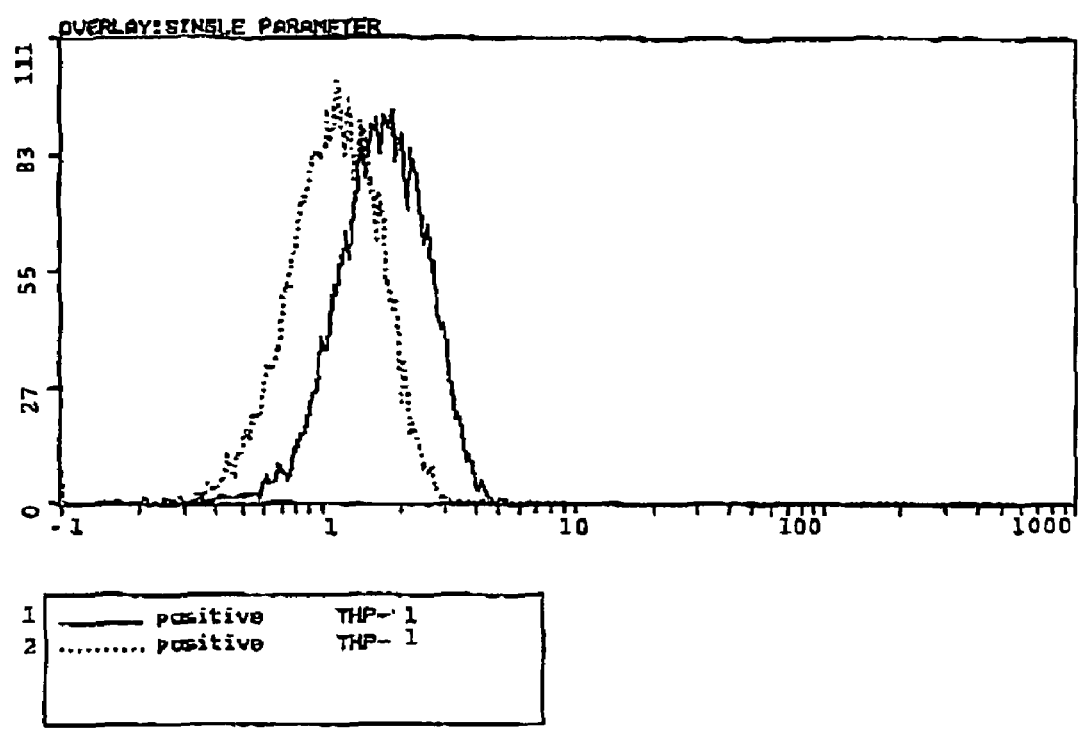

Results:

According to FACS analysis with biotin-labeled αMSH, unstimulated THP-1 cells express significant amounts of binding sites which are specific for αMSH compared with control mixtures incubated only with FITC-streptavidin. The concentration of αMSH employed in this experiment was $10^{-10}$ M (see FIG. 5).

In order to determine whether THF-1 cells express one of the known melanocortin receptors (MC), RT-PCR was carried out with MC-1-, MC-2-, MC-3- and MC-4-specific primers. Total RNA was obtained from THP-1 cells. A PCR product specific for MC-1 with an expected length of 416 bp was detected (Rajora et al., 1996, J. Leuk. Biol., 59, 248). PCR products specific for MC-2, MC-3 or MC-4 were not detected. The results show that THP-1 cells express MC-1 which, in contrast to other melanocortin receptors, is specific for αMSH and ACTH.

In order to investigate whether the binding sites expressed on THP-1 are specific for αMSH, competition experiments were carried out with αMSH or KPV or KPT.

The specific binding was measured by incubating THP-1 cells with biotin-labeled αMSH ($10^{-10}$ M) and various concentrations of unlabeled αMSH or peptides. Unlabeled αMSH in a concentration of $10^{-8}$ significantly suppressed αMSH binding. No significant suppression was observable when αMSH was employed in concentrations of $10^{-6}$ M, $10^{-10}$ M or $10^{-12}$ M (FIGS. 6a to 6d).

When unlabeled KPV was employed, a significant inhibition was observable only at a concentration of $10^{-6}$ M (see FIGS. 7a to 7d).

In the case of the peptide KPT, a significant inhibition of αMSH binding was observable at each of the tested concentrations ($10^{-6}$ to $10^{-12}$ M, see FIGS. 8a to 8d).

These results show that the KPT peptide binds to the melanocortin receptor on THP-1 cells which is specific for αMSH, which indicates that αMSH and KPT have a common binding site. However, since KPT shows competition for the receptor even at very low concentrations, it is probable that this peptide in fact has a higher affinity for the MC-1 receptor than MSH.

EXAMPLE 4

Material and Methods:

Human dermal microvascular endothelial cells (HDMEC) and the cell line HMEC-1 (human microvascular endothelial cell line 1) were treated either with TNFα or LPS in the presence or absence of one of the peptides. The cells were harvested for RNA isolation after 3 and after 6 hours after treatment or harvested either for adhesion molecule EIA or FACS analysis 3, 6, 16 or 24 hours after treatment. RNA underwent reverse transcription, and samples were subjected to a PCR for E selectin, ICAM-1, VCAM or for β-actin as housekeeping gene in order to carry out a semiquantitative determination. For the lymphocyte adhesion assay, the endothelial cells were seeded in dishes and incubated with $^{51}$Cr-labeled lymphocytes. After a washing step, the amount of remaining lymphocytes bound to the EC layer was determined by measuring the radioactivity in the samples.

Results:

Treatment of the endothelial cells with αMSH or KPT inhibited the LPS- or TNFα-induced expression of adhesion molecules. This effect was observed in a concentration range from $10^{-6}$ to $10^{-12}$ αMSH or peptide. The peptide KPT had the strongest effect on the expression of adhesion molecule mRNA.

The LPS- or TNFα-induced surface expression of adhesion molecules was reduced to a small extent by all the agonists. These data were obtained both by EIA, in which case whole cells were employed, and by FACS with specific antibodies (see, FIG. 9a, which shows EIA data).

αMSH significantly reduces the binding of T and B cells to LPS- or TNF-αMSH-treated EC layers (see FIG. 9b). Taken together, these results show that αMSH has an effect on the adhesion of lymphocytes to EC and thus also reduces the extravasation of lymphocytes in conditions of tissue inflammation. This is supported by the in vivo data on localized vasculitis.

EXAMPLE 5

Material and Methods:

Epidermal cells (ECs) or normal human keratinocytes (HNK) were treated with IL-1, LPS or TNFα in the presence or absence of peptides. After 15 or 30 minutes, the nuclear proteins were obtained and subjected to an electrophoretic mobility shift assay (EMSA) with radiolabeled oligonucleotide with NF-κB-specific binding sequence. Unlabeled oligonucleotide was used as competitor. In some experiments, antibodies against the p65 or p50 chain of NF-κB were used in order to confirm the identity of the detected bands as either p50 homodimer or p50/p65 heterodimer.

Result:

Addition of the peptides in TNFα- or LPS-treated ECs and in IL-1-treated HNKs leads to a reduced activation of the transcription factor NF-κB (see FIGS. 10 and 13a). This in turn leads to a diminution in the transcription of the genes for numerous proinflammatory mediators (cytokines, chemokines, adhesion molecules, etc.). The identity of the observed bands in the EMSA as NF-κB heterodimer was confirmed by using anti-p65 antibody.

EXAMPLE 6

Material and Methods:

Mice were treated with LPS by s.c. injection on one ear. This preparatory injection induces a long-lasting rise in E selectin expression at the site of the LPS injection. 24 hours later, a second LPS dose was injected i.p. (challenge). This second LPS injection leads to rapid vessel necrolysis and to the formation of petechial lesions which are easily measurable because of their size and number. αMSH (25 μg) was administered at the time of the preparatory LPS injection.
Result:
Injection of αMSH at the time of the preparatory LPS administration inhibits the induction of local E selectin expression in the ear (see FIG. 11a) and significantly reduces the number and size of the petechial lesions formed after the challenge injection of LPS (see FIG. 11b).

EXAMPLE 7

Material and Methods:
Bone marrow dendritic cells (BMDC) were isolated from the femoral bones of mice and treated with IL-4 and GM-CSF for 6 or 9 days. On day 6 or 9, the cells were treated with αMSH ($2 \times 10^{-11}$ M) or the peptide KP ($2-10^{-6}$ M) 3 hours and 2.5 hours before reinjection into naïve mice with the same genetic background. 2 hours before reinjection, the cells were treated with hapten (1 mM DNBS, the water-soluble form of DNFB). Immediately before the reinjection, the cells were washed 2× with PBS. $5 \times 10^{-5}$ cells were injected i.v. into each animal. Control cells were treated either with DNBS alone or with αMSH alone or were left untreated. 5 days after injection, the animals were contacted with DNFB on the ear, and the ear thickness was measured the next day. 2 weeks later, the animals were resensitized with DNFB and again recontacted on the ear 5 days later. Finally, the auricular swelling was measured.
Results:
Recipient animals injected with untreated cells or αMSH-treated cells showed no immune response after the first challenge, as expected. Recipient animals injected with DNBS-treated BMDC showed an appropriate CHS reaction at the time of the first challenge. This reaction was suppressed in animals injected with cells previously treated with TNBS and αMSH or TNBS and KP in vitro. Thus, contact of DCs with αMSH or peptide is sufficient to induce inhibition of CHS (see FIG. 12).
At the time of the second challenge and of the corresponding resensitization, animals again injected with DNBS-treated cells showed no immune response, whereas animals injected with DNBS/αMSH-treated cells showed no immune response, which indicates that the αMSH-induced tolerance is likewise mediated by DC (see FIG. 12).

EXAMPLE 8

"Immunotherapy with αMSH or αMSH-Derivative-Treated Dendritic Cells or T Cells"

Dendritic cells (DC) were isolated (from blood, bone marrow or tissue). It is, however, also possible to use cell mixtures containing DC (e.g. epidermal cell mixtures) and cultivated in the presence of GM-CSF and IL-4 (preferably: 250-1000 μ/ml for each of the substances).

After a maturation period (preferably 6-9 days), the cells are loaded with antigen (concentration depends on the particular antigen, likewise period) and treated with αMSH or derivatives thereof. The derivatives correspond at least to amino acids 12 and 13 of αMSH (Lys-Pro), with preference for Lys-Pro-Val-containing derivatives. D and L configurations of the AA are possible, likewise conservative AA exchanges. This leads inter alia to the possibility also of using Lys-Pro-Thr which is derived; from IL-1β, and derivatives thereof with N-terminal extensions. Derivatives with C-terminal extensions can also be employed. Addition of the peptide can take place before addition of the antigen, at the same time, later, once or more than once (the preferred dose depends on the particular peptide, for αMSH e.g. $10^{-8}$ M to $10^{-14}$ M).

The cells treated in this way are then injected i.v. into the recipient organism (i.p. or s.c. would also be possible); mouse: $2 \times 10^5$ cells approximate lower limit. Depending on the antigen, it is sufficient to undertake a single injection or necessary to undertake a plurality of injections in this case. It is also possible that the injections need to be repeated after lengthy periods (no data yet available on this).

An alternative possibility is to bring DC into contact with T cells outside the body and then to inject the mixture or the T cells. In this case, the antigen loading of the DC can take place before the contact with the T cells or during it. The T cells may moreover originate from individuals which have already been sensitized to the particular antigen. The lower limit in the mouse is about 1 million T cells, with more cells being preferred (FIGS. 14 and 15).

Advantages of such a mode of use are the prevention of every type of unwanted immune response, which are antigen-specific and in which antigen-specific lymphocytes (B or T cells) play a pathogenetic part. These include inter alia allergies, autoimmune diseases, chronic inflammations or implantations. A cure of preexistent disorders is also possible if sufficiently large numbers of cells are employed.

The surprising results can, without wishing to be bound to one theory, be regarded as the fact that αMSH is a potent immunomodulator and has numerous antiinflammatory properties. These include inter alia its property of reducing the expression of costimulatory molecules on DC. Similar properties are also shown by the αMSH derivatives of the invention, including the C-terminal tripeptide and the dipeptide Lys-Pro. Derivatives with a different amino acid composition (conservative AA exchanges) also have comparable properties, and these include in particular the Lys-Pro-Thr derived from IL-1β (so that it is to be presumed that N-terminally (analogous to αMSH) extended peptides with sequence colinear to IL-1β have the same effect).

αMSH, as well as the derivatives, are able to induce hapten-specific tolerance in vivo. DC are professionally antigen-presenting cells which are able to induce numerous types of immune responses and which also determine the course of such responses. These immune responses include in particular the T-cell-mediated immune responses.

It has now been possible to show that in vitro treatment of DC or DC/T cell mixtures with an antigen in the presence of αMSH or derivatives leads to the cells likewise inducing hapten-specific tolerance after injection into an organism.

The mechanism in this case appears to be that the antigen presentation by the DC is modulated by αMSH or derivatives in such a way that suppressor T cells are generated. It was thus possible to show that T cells in appropriate mixtures show high expression of CTLA-4 (FIG. 16). This is one of the surface molecules which characterize suppressor T cells.

It is possible with DC or T cells generated in this way to preventively impede autoimmune diseases, chronic inflammations or allergies. A cure of a preexistent pathological condition is also conceivable if sufficiently large numbers of cells are used.

The compounds of the invention can also be used for tumor treatment by means of an in situ activation of dendritic cells. It is also possible that this method can be used for tolerization in the presence of the peptides of the invention.

The invention claimed is:

1. A method for treatment of ulcerative colitis by administering to a patient in need of such treatment, a pharmaceutical composition comprising a therapeutically effective amount of a compound selected from the group consisting of Lys-(D)Pro-Thr (K(D)PT), N-acyl Lys-(D)Pro-Thr, C-amide Lys-(D)Pro-Thr, and C-esters of Lys-(D)Pro-Thr; or a pharmaceutically acceptable salt of said compound, wherein said therapeutically effective amount is in the range from 20 μg/kg of body weight to 10 mg/kg of body weight.

2. The method of claim 1, wherein said therapeutically effective amount of the compound of the formula (I) is 100 μg/kg of body weight to 1 mg/kg of body weight.

3. The method of claim 1, wherein said compound is the tripeptide Lys-(D)Pro-Thr.

4. The method of claim 1, wherein said compound is any one of N-acyl Lys-(D)Pro-Thr, C-amide Lys-(D)Pro-Thr, or C-esters of Lys-(D)Pro-Thr.

* * * * *